(12) United States Patent
Karimov et al.

(10) Patent No.: US 10,842,631 B2
(45) Date of Patent: Nov. 24, 2020

(54) TRANSCATHETER CARDIAC DE-AIRING SYSTEM

(71) Applicant: THE CLEVELAND CLINIC FOUNDATION, Cleveland, OH (US)

(72) Inventors: Jamshid Karimov, Cleveland Heights, OH (US); Marc Gillinov, Cleveland, OH (US); Kiyotaka Fukamachi, Mayfield Heights, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 120 days.

(21) Appl. No.: 15/903,737

(22) Filed: Feb. 23, 2018

(65) Prior Publication Data

US 2018/0235759 A1  Aug. 23, 2018

Related U.S. Application Data

(60) Provisional application No. 62/462,614, filed on Feb. 23, 2017.

(51) Int. Cl.
*A61F 2/24* (2006.01)
*A61B 17/12* (2006.01)
*A61M 25/10* (2013.01)
*A61B 17/00* (2006.01)

(52) U.S. Cl.
CPC ...... *A61F 2/2481* (2013.01); *A61B 17/12136* (2013.01); *A61B 2017/0023* (2013.01); *A61B 2017/00084* (2013.01); *A61B 2017/00132* (2013.01); *A61B 2017/00154* (2013.01); *A61B 2017/00212* (2013.01); *A61B 2017/00243* (2013.01); *A61B 2017/00292* (2013.01); *A61B 2017/00557* (2013.01); *A61B 2017/00778* (2013.01); *A61F 2002/2484* (2013.01); *A61F 2250/0003* (2013.01); *A61M 25/10* (2013.01);
(Continued)

(58) Field of Classification Search
CPC ........... A61F 2/2481; A61F 2250/0003; A61B 17/12136; A61B 2017/00557; A61B 2017/00243; A61B 2017/00212; A61B 2017/00154; A61B 2017/00132; A61M 2025/1072; A61M 25/10
USPC ....................................................... 606/191
See application file for complete search history.

(56) References Cited

U.S. PATENT DOCUMENTS 3,034,501 A  5/1962 Hewson
3,053,249 A  9/1962 Smith
(Continued)

FOREIGN PATENT DOCUMENTS

WO  97/40751 A1  11/1997

OTHER PUBLICATIONS

PCT International Search Report for corresponding International Application No. PCT/US2018/019461, dated May 25, 2018, pp. 1-12.

*Primary Examiner* — George J Ulsh
*Assistant Examiner* — Andrew P. Restaino
(74) *Attorney, Agent, or Firm* — Tarolli, Sundheim, Covell & Tummino LLP

(57) ABSTRACT

Systems and methods for de-airing a cardiac chamber during cardiac surgery are provided. A catheter-based inflatable device is inserted adjacent a target area of the heart, and the frequency of inflation and deflation of the inflatable device is controlled via a remote controller to change the shape of the cardiac chamber to dislodge air bubbles from their deposition site in the cardiac chamber.

19 Claims, 7 Drawing Sheets

(52) U.S. Cl.
CPC ............... *A61M 2025/1072* (2013.01); *A61M 2025/1088* (2013.01)

(56) References Cited

U.S. PATENT DOCUMENTS

| | | | |
|---|---|---|---|
| 4,962,758 A * | 10/1990 | Lasner | A61H 23/0218 601/148 |
| 5,119,804 A | 6/1992 | Anstadt | |
| 5,290,257 A | 3/1994 | Zhong | |
| 5,385,528 A | 1/1995 | Wilk | |
| 6,059,750 A | 5/2000 | Fogarty et al. | |
| 6,238,334 B1 | 5/2001 | Easterbrook, III et al. | |
| 6,953,438 B2 | 10/2005 | Milo | |
| 8,876,850 B1 * | 11/2014 | Vollmers | A61M 25/04 606/194 |
| 2004/0167563 A1 * | 8/2004 | Fogarty | A61M 1/1068 606/192 |
| 2007/0299475 A1 * | 12/2007 | Levin | A61M 25/10181 607/9 |
| 2008/0275295 A1 * | 11/2008 | Gertner | A61B 17/00234 600/37 |
| 2009/0171278 A1 * | 7/2009 | Hirszowicz | A61M 25/1006 604/97.01 |
| 2010/0274164 A1 | 10/2010 | Juto | |
| 2010/0318114 A1 * | 12/2010 | Pranevicius | A61M 25/10 606/194 |
| 2011/0015738 A1 * | 1/2011 | Vaingast | A61F 2/0036 623/14.13 |
| 2011/0245750 A1 | 10/2011 | Lynch et al. | |

\* cited by examiner

TRANSCATHETER CARDIAC DE-AIRING SYSTEM

CROSS-REFERENCE TO RELATED APPLICATIONS

The present application claims priority to U.S. Provisional Application No. 62/462,614 filed on Feb. 23, 2017, the entirety of which is incorporated by reference herein.

GOVERNMENT FUNDING

This invention was made with government support under HL119810 awarded by the National Institutes of Health. The government has certain rights in the invention."

TECHNICAL FIELD

Systems and method for de-airing the heart to prevent or mitigate air embolisms are provided.

BACKGROUND

Cardiac surgery procedures generally involve establishing access to the heart and its internal structures to perform repair. The heart's chambers are naturally filled with blood, and once accessed from outside during medical procedures, some amount of air can enter the heart and lodge inside the chambers. Air embolisms frequently arise from cardiac surgery and can cause significant complications such as cardiac arrest and stroke. Rapid recognition and intervention is important for reducing morbidity and mortality. Significant progress has been made in intra-operatively visualizing cardiac chambers using transesophageal echocardiography (TEE). However, there is no established technique or dedicated device that could prevent or mitigate air embolism during cardiovascular surgical procedures and interventions.

The standard air-removal methods during heart surgery are based on conventional techniques such as manual manipulating the heart via gentle massage or compression to mobilize air deposited on cardiac walls and between cardiac chambers. The surgeon uses TEE to visualize air bubbles as they dislodge and dissipate. Other methods that have been utilized are using elongated forceps or suction tips to reach into the heart and push the cardiac wall to generate motion. Such methods, however, have not been proven to be safe. Other methods to manage air entrapment inside the cardiac chamber include shaking the patient's body, $CO_2$ insufflation, and surgical position change. However, there is little to no evidence of sustained reduction of embolism with $CO_2$, and currently utilized surgical position changes do not decrease the cerebral microembolic load compared with the horizontal head position. Further, existing methods focus primarily on air-suction techniques through vents placed in the aorta or ventricle. These techniques are primitive and extremely time consuming. No known method addresses air dislodgement inside the heart, which appears to be a primary reason why air, once entrapped within the heart, does not move easily creating "pools" of air, which are even harder to manage. The existing techniques are even less feasible in minimally invasive cardiac surgery (MICS) than in a standard setting due to limitations in incision size in minimally invasive procedures (e.g. 4 to 7 cm incision length), which limits any manual access to the heart. Because intracardiac air rapidly changes its locations and appearance, timely intervention to remove air is critical, especially before weaning from a cardiac bypass machine. For this reason, cardiac de-airing systems and method are needed to protect against complications associated with cardiac surgery.

SUMMARY

Systems, devices and methods for de-airing the heart during cardiac surgery are provided. Systems generally included a catheter-based inflatable device that is sized and configured to be placed in contact with the heart and that is controlled by an external remote controller. Systems utilize active inflation and deflation of the inflatable device. The inflatable device transmits motion to the heart thereby dislodging entrapped intracardiac air, which can be eventually evacuated through a cardiac incision or vent placed in the heart or a major cardiac blood vessel.

In an embodiment, a system for de-airing a heart in a patient is provided. The system comprises a catheter and inflatable device coupled to the catheter. In an active state, the inflatable device is sized and configured to transmit motion to the patient's heart sufficient to change the shape of the heart. The system also includes a remote controller comprising a power source and a processor. The processor is configured to control inflation parameters of the inflatable device. The system also includes a flow control valve in communication with the remote controller and the inflatable device.

In another embodiment, a method for de-airing a heart in a patient is provided. The method includes inserting a catheter coupled to an inflatable device into a thoracic cavity of a patient. The method further includes positioning the catheter adjacent to the patient's heart.

The method also includes placing the inflatable device between the heart and the pericardium or into a cardiac chamber of the heart and then inflating the inflatable device. The method additionally includes controlling the frequency of inflation and deflation of the inflatable device via a remote controller comprising a power source and a flow control valve. The method further includes changing the shape of the heart via the controlling step to dislodge air bubbles from their deposition site in the heart.

DETAILED DESCRIPTION

Figure 1:
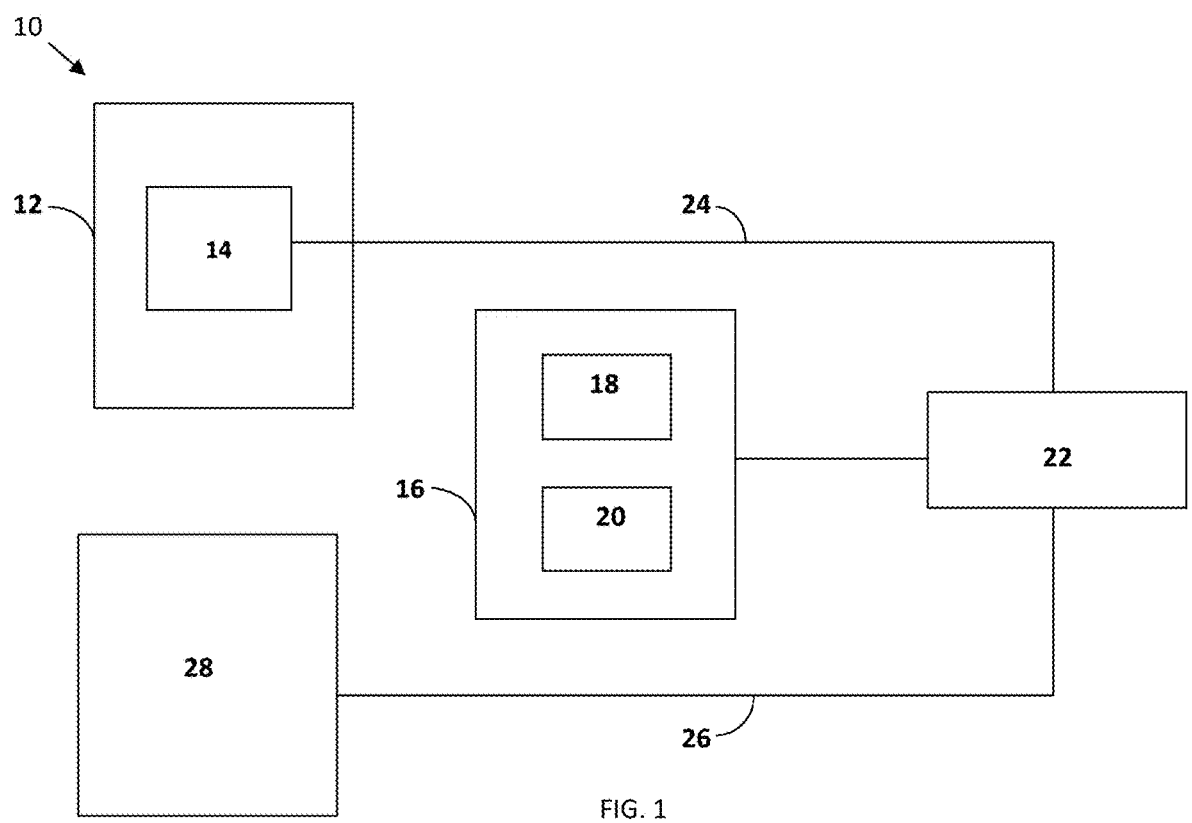
FIG. 1 is a block diagram of a system according to an embodiment of the present disclosure.

As used herein with respect to a described element, the terms "a," "an," and "the" include at least one or more of the described element including combinations thereof unless otherwise indicated. Further, the terms "or" and "and" refer to "and/or" and combinations thereof unless otherwise indicated. It will be understood that when an element is referred to as being "over," "on," "attached" to, "connected" to, "coupled" with, "contacting," "in communication with," etc., another element, it can be directly over, on, attached to, connected to, coupled with, contacting, or in communication with the other element or intervening elements may also be present. In contrast, when an element is referred to as being "directly over," "directly on," "directly attached" to, "directly connected" to, "directly coupled" with, "directly contacting," or in "direct communication" with another element, there are no intervening elements present. An element that is disposed "adjacent" another element may have portions that overlap or underlie the adjacent element. By "substantially" is meant that the shape, configuration, or orientation of the element need not have the mathematically exact described shape, configuration or orientation but can have a shape, configuration or orientation that is recognizable by one skilled in the art as generally or approximately having the described shape, configuration, or orientation. The term "inactive configuration" or "inactive state' as used with respect to an inflatable device refers to the configuration of the inflatable device in a completely deflated state. The term "active configuration" or "active state" refers to the configuration of the inflatable device when it has been at least partially inflated such that it can transmit motion to the heart to change the shape of the heart. When referring to a surgical procedure, the term "during" the surgical procedure includes any peri-operative period of surgery, including after the surgical procedure.

The present disclosure is directed to systems, devices, and methods for de-airing the heart to prevent or mitigate air embolisms. Such systems, devices and methods can prevent or decrease complications of cardiac surgery. Systems and methods include an inflatable device that is sized and configured to be inserted into the thoracic cavity via a catheter in an inactive configuration and to transmit motion to the patient's heart sufficient to change the shape of heart in an active state.

The inflatable device can be introduced temporarily under the heart between the inferior cardiac surface and pericardium, for example, during or after a surgical procedure to allow cardiac re-positioning and thereby cardiac de-airing. For example, the device can be sized and configured to "wiggle" the heart thereby dislodging any entrapped intra-cardiac air. The dislodged air can then be captured by a dedicated suction vent or can exit through an incision. A catheter can be used to place the inflatable device adjacent the heart and can be introduced not only through small incisions but also through keyhole incisions and ports placed through the chest. As such, the inflatable device can be used during MICS, although systems and method as disclosed herein can be used for other types of surgeries as well. The inflatable device can be in fluid communication with an inflation source (e.g. a fluid or gas) that can be introduced into the inflatable device at desired parameters to cause an intended geometrical change of the heart. Air and vacuum sources can be external to the inflatable device. For example, air and vacuum sources that are standard in the operating room can provide the inflation medium or vacuum source. Alternatively, the inflation medium or vacuum source can be incorporated within components of systems disclosed herein, such as the remote controller as described in more detail below.

Referring to FIG. 1, an embodiment of a system for de-airing the heart in a patient is provided. System 10 comprises a catheter 12, an inflatable device 14 coupled to catheter 12, and a remote controller 16 comprising a power source 18 and a processor 20. Processor 20 is configured to control inflation parameters of the inflation device. System 10 also includes a flow control valve 22 in communication with remote controller 16 and inflatable device 14. As illustrated in FIG. 1, a first flow line 24, such as tubing, can be connected to flow control valve 22 at one end and inflatable device 14 at another end. A second flow line 26, which can also be tubing, can be connected to flow control valve 22 at one end and an inflation/deflation source 28 at another end.

Figures 2A, 2B:
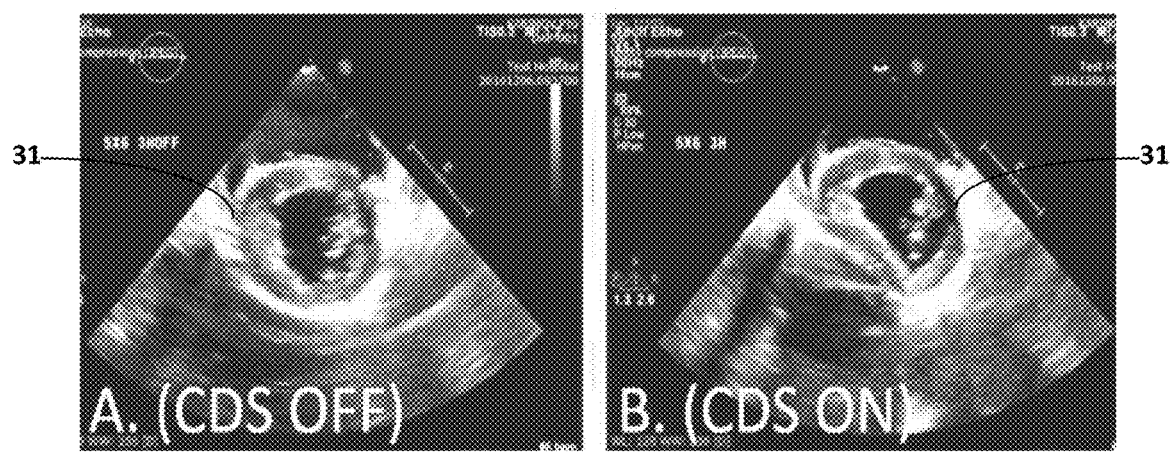
FIGS. 2A and 2B are TEE images of the heart when the inflated device is in an inactive state and an active state respectively.

Regarding further details of the inflatable device, when activated, the device is sized and configured to transmit motion to the patient's heart sufficient to change the geometric configuration or shape of the heart. Such changes in the geometric configuration of the heart include changes in the overall shape, volume, or length of the heart or its chambers. For example, FIG. 2 is an image of a TEE depicting the heart 31 when the inflatable device is in an inactive state (FIG. 2A) and when the inflatable device is in an activated state (FIG. 2B). As can be seen from these figures, when the inflatable device is inactive, heart 31 has a generally round configuration. However, when the inflatable device is activated, the shape of heart 31 is modified to a more oval configuration. The above figures are only exemplary and the heart can take on other shapes or various degrees of deformation after the inflatable device transmits motion to the heart such as, for example, a substantially flattened configuration or a slightly deformed (non-round) configuration.

Figure 3A:
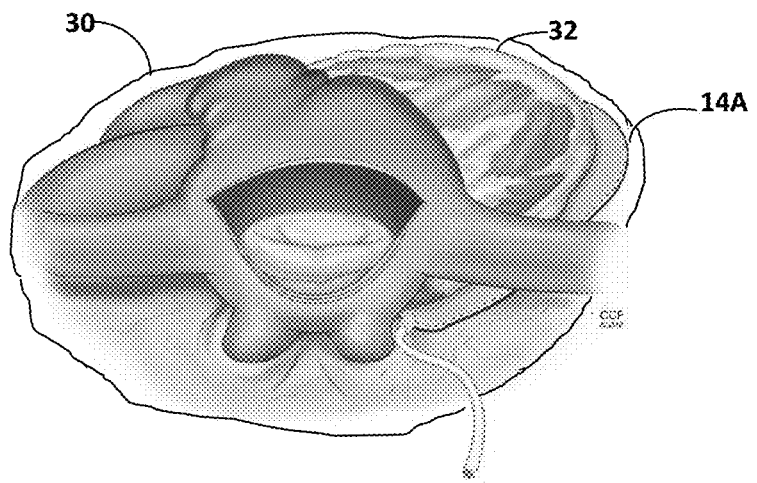
FIGS. 3A and 3B are perspective views of an inflatable device according to an embodiment of the present disclosure in an active state and an in active state, respectively.
Figure 3B:
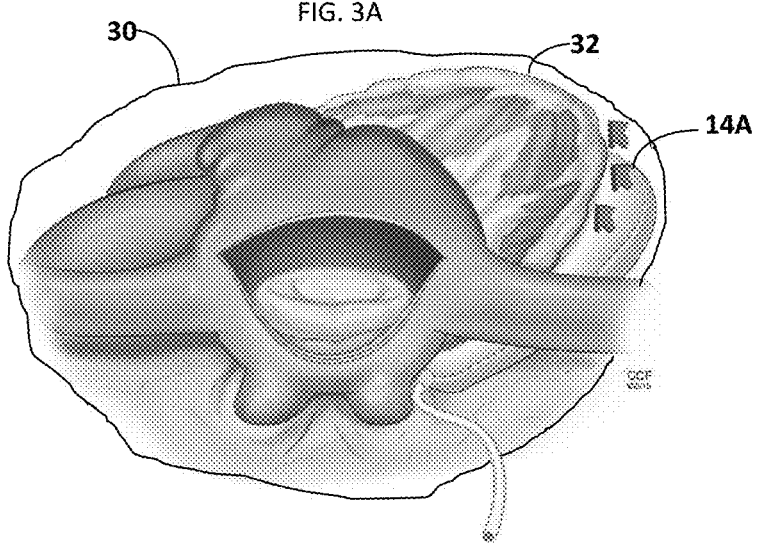

FIGS. 3A and 3B illustrate inflatable device 14A in an inactive and active state, respectively. Inflatable device 14A is preferably sized and configured to be positioned in the pericardium sac between the pericardium 30 and the heart 32. In particular the inflatable device is sized and configured such that adjusting the volume of the inflatable device, for example, effectively lift the heart to re-position the heart inside the thoracic cavity. Such volume adjustment can also properly secure the inflatable device between the pericardium and heart. The pericardium surrounding the heart can also assist in device fixation and can contribute to the inflatable device's efficacy because the pericardium constrains the heart, limiting cardiac movement since the heart's position is defined by the pericardial sac.

Figure 4:
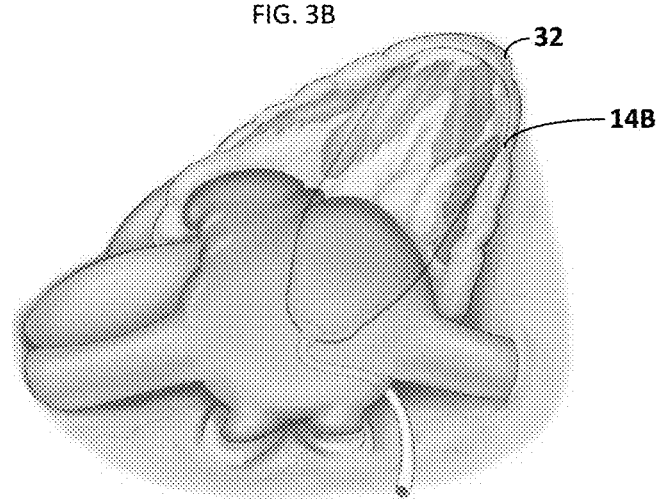
FIG. 4 is a perspective view of an inflatable device according to an embodiment of the present disclosure.
Figure 5:
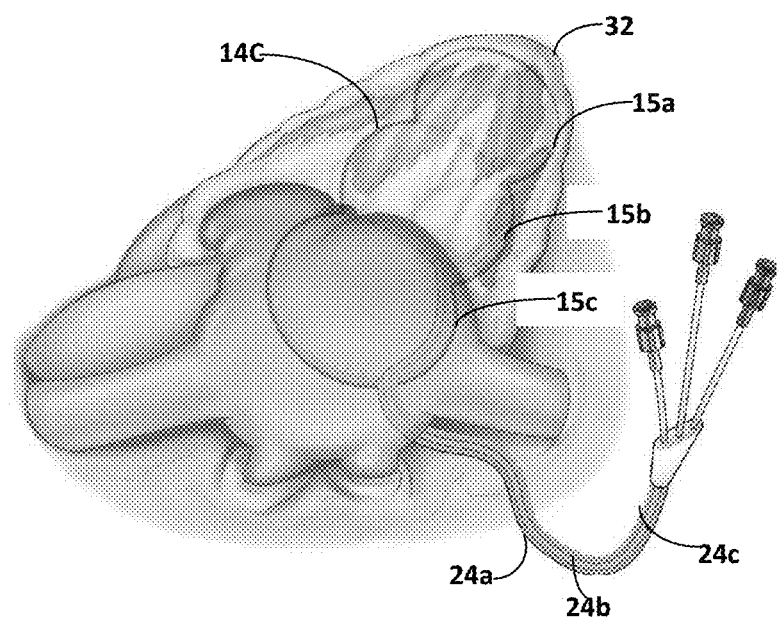
FIG. 5 is a perspective view of an inflatable device according to an embodiment of the present disclosure.

The inflatable device can take various forms. For example, the inflatable device can be a balloon, a bladder, a cushion, a ball or any other dedicated inflatable/deflatable unit that can be introduced adjacent to the heart via a catheter. The inflatable device can also be part of a kit that includes inflatable devices of different sizes to accommodate both pediatric and adult patients. Further, the device can be a single, dual, or multi-chamber unit. FIG. 4 illustrated a single elongated inflatable device 14B while FIG. 5 illustrates a multi-chamber, segmented inflatable device 14C.

Figure 6:
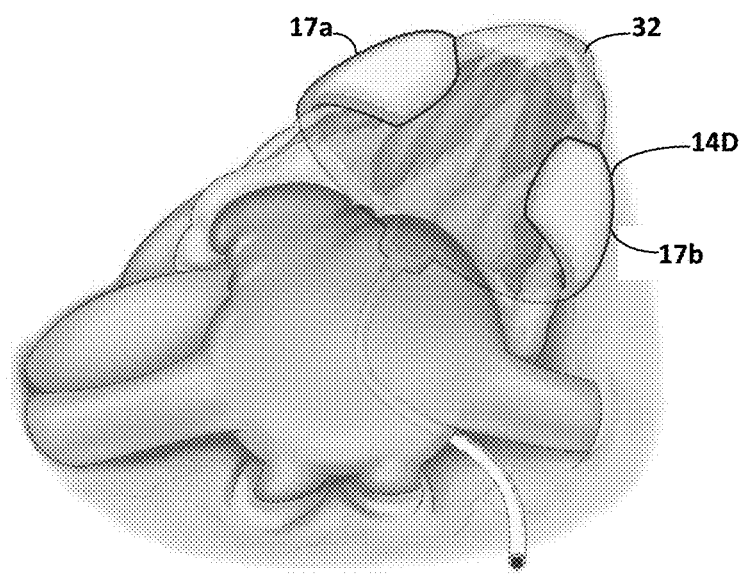
FIG. 6 is a perspective view of an inflatable device according to an embodiment of the present disclosure.
Figure 7:
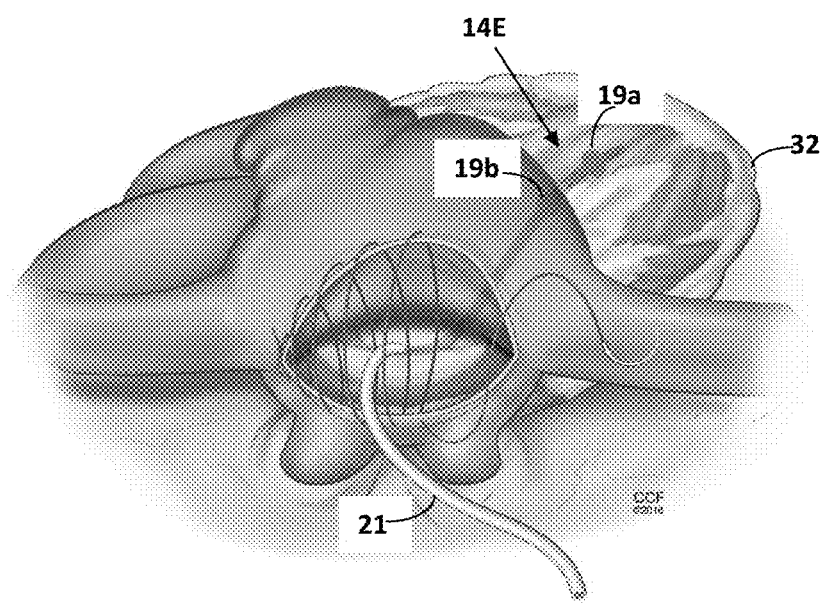
FIG. 7 is perspective view of an inflatable device according to an embodiment of the present disclosure.

Each segment 15 of inflatable device 14C can be in fluid communication with a separate flow line 24a, 24b and 24c such that each segment can be selectively and independently activated. Although FIG. 5 depicts multiple segments of a single balloon, the inflatable device can comprise multiple balloons or other types of inflatable devices. The inflatable device can have different shapes such as, for example, round, bullet-shaped, rhomboid, square, rectangular, or starfish-shaped. Referring to FIG. 6, in certain embodiments, inflatable device 14D is cuff-shaped and has arms 17 that can be selectively inflated to alternate the movement of different sides of the heart. With any configuration of an inflatable device that includes independent and selectively inflatable portions, one part of the device can be inflated while another portion is deflated either simultaneously or sequentially. Referring to FIG. 7, the inflatable device 14E can comprise one or more inflatable members 19 that are sized and configured to be inserted inside a patient's heart, such as a cardiac chamber. Such an embodiment of an inflatable device causes motion of intracardiac blood to dislodge air pools and smaller air depositions inside a ventricle. Such an embodiment can also include a suction line 21 to a vent, such as a left ventricular vent used in standard cardiac bypass procedures, for example. In certain embodiments, the inflatable device an inflation thickness of between about 18 millimeters (mm) and 40 millimeters in an active state.

The inflatable devices as described herein are sized and configured differently than other inflatable devices used in vascular procedures, such as angioplasty balloons. Angioplasty balloons can be used only in a circular environment, such as blood vessel. Blood vessels are needed to provide a delivery path for the catheter for angioplasty balloons. Without the vessel, angioplasty balloon cannot be delivered. As such, angioplasty balloons can be used only inside the vessel and are too small in terms of length, diameter and surface area, for example, to generate enough force to transfer any motion to the heart. Further, inflation and deflation of inflation devices as described herein can create a motion amplitude that is transmitted to the heart. This is generally achieved by changing the "thickness" of the device through inflation. Angioplasty balloons cannot achieve such an amplitude due to size and design limitations.

The inflatable device can have a textured surface, such as tangs, teeth or other types of protrusions that create friction or fixation between the implantable device and the heart and the pericardium, the two surfaces between which the inflatable device can be placed. Such a textured surface can promote easy insertion and removal of the inflatable device and also prevent the inflatable device from dislodging in an undesirable direction. For example, in one direction, such as the from the incision site towards a placement site under the heart, the device can be easily inserted. However, when the heart resumes beating or when other physiological movement occurs such as breathing, any lateral movement of the implantable device can be prevented as the textured surface prevents or minimizes slippage through friction between the two interfaces involved: the heart/device interface and the pericardium/device interface.

As referenced above, the inflatable device can be inserted via a catheter through a patient's chest wall including through small working ports placed in the patient's intercostal space. For example, the inflatable device can be coupled to a catheter and the catheter can be inserted into the thoracic cavity via an outer sheath. As such, the inflatable device can be fabricated from a flexible, deformable material so that the inflatable device can be contained within an outer sheath in an inactive state and can assume an active state once deployed from the outer sheath. Such a flexible, deformable material also allows the inflatable device (and any connecting tubing or flow lines) to be inserted through keyhole incisions or ports and also to be easily removed from the surgical field by pulling the device in a proximal direction through the ports. Non-limiting examples of fabrication materials include nylon, PTA, PTFE, polyethylene, polyurethane, and thermo-sensitive materials such as thermoplastic polymers. Preferably, the inflatable device is only attached to the distal end of the catheter such that it is essentially free-forming as opposed to being attached to the middle of the catheter shaft resulting in limited radial expansion.

The inflatable device can also have other features. For example, an inflatable device can include suction cups or ports that attach the device to the heart or pericardial surface via negative pressure for vacuum fixation to the heart. An inflatable device can also include temperature sensors to determine the temperature of the heart or surrounding structures, as described in more detail below. The inflatable device can also have a fixation member that cooperates with a complimentary fixation member of the catheter to be detachable from the catheter and/or re-positioned if necessary. For example, the inflatable device can have a gooseneck that removably attaches to a connector on the catheter.

In addition to transferring motion to the heart to dislodge air bubbles, the inflatable device can serve other functions as well. For example, the inflatable device can be used to stabilize or dampen physiologic motion when necessary during a cardiac surgical procedure.

The inflatable device can also be used to regulate heart temperature be adjusting the temperature of the inflation medium used to inflate the device. Heart temperature is important for cardiac protection if hypothermia is used during operation or during heart re-warming.

Figure 8:
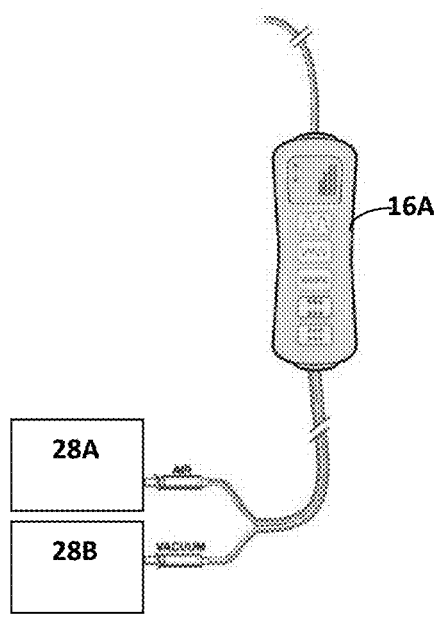
FIG. 8 is a top view of a remote controller attached to inflation/deflation sources according to an embodiment of the present disclosure.

A remote controller can be in communication with the inflatable device and is external to the patient's body. The remote controller can be a hand-operated pump, another type of mechanical unit, an electronic control unit, or combinations thereof. The remote controller device 16A can be a handheld device with a user interface as illustrated in FIG. 8 that is not linked to the inflatable device through a rigid assembly. As such, the inflatable device can be controlled remotely, which reduces the risk of injury caused by additional components that are close to the heart. The remote controller itself may contain the inflation medium, such as having a gas or fluid source incorporated within a housing of the remote controller. Alternatively, the remote controller can be in communication with a gas or fluid source 28A or a vacuum source 28B readily available in the operating room and can regulate the inflation/deflation rate of the inflatable device via flow control valves, as described in more detail below.

The remote controller comprises a processor configured to control inflation parameters of the inflatable device. The processor can include a microprocessor and includes the necessary electronic circuitry and software to control the inflation parameters of the inflatable device.

Non-limiting inflation parameters include the onset of inflation/deflation, the duration of inflation/deflation, the frequency of inflation/deflation, and the amplitude of the inflation. The remote controller can be programmed to deliver pressurized fluid, gas or other inflation medium to the inflatable device at a certain desired frequency. The desired frequency can be achieved by the frequency of opening and closing the flow control valves, such as solenoid valves, that regulate air or fluid flow resulting in inflation of the inflatable device or suction or vacuum resulting in deflation of the inflatable device. In certain embodiments, the remote controller can be manually programmed by the operator or pre-programmed to inflate or deflate the inflatable device at a pre-determined frequency. Such frequency can be regulated, for example, by controlling the speed of injection of the inflation medium into the inflatable device, the amount of inflation medium injected into the inflatable device, and the duration of injection of the inflation medium to the inflatable device. The remote controller can also be programmed to deliver the inflation medium at different pressure ranges, such as pre-determined pressure values so that the operator can shape the inflatable device as required to mobilize the heart and achieve a desired geometric change of the heart. As such, the remote controller can include or be in communication with a pressure regulator or valve to maintain the desired pressure within the inflatable device as well as to avoid over-inflation, which can cause excessive compression during use. The remote controller can be programmed to activate the inflatable device (or segments thereof) based on a pre-determined activation pattern of inflation and deflation. Non-limiting examples of inflation parameters are frequencies under 1 kHz, more preferably between about 1 Hz and about 100 Hz and more preferably between about 2 Hz and 10 Hz. In certain embodiments, the frequency is not above about 30 to about 40 Hz.

The remote controller can also be programmed to automatically adjust inflation parameters based on feedback measurements of the state of inflation of the inflatable device to maintain a certain level of inflation/deflation or to maintain an inflation/deflation pattern that achieves an adequate displacement of the heart to dislodge air bubbles. The remote controller can provide additional feedback to the operator on activation of the system, deactivation, or activation or operation failure.

Systems can be instrumented to obtain measurements such as balloon volume and working parameters such as inflation, deflation and dwell time of the inflatable device; feedback on system activation, deactivation, troubleshooting, and potential failure (such as, for example, low/high air pressure, or low/high vacuum). Such measurements can be obtained from pressure release valves with pressure sensors to detect air pressure. Such measurements can be relayed to the remote controller so that the remote controller can display the status of the system on the display screen of the user interface.

The remote controller can be set to work continuously, intermittently, as desired by the operator, according to the intra-operative clinical setting, or according to pre-set device operation modes. The remote controller also includes a power source, which can be a battery.

Figure 9:
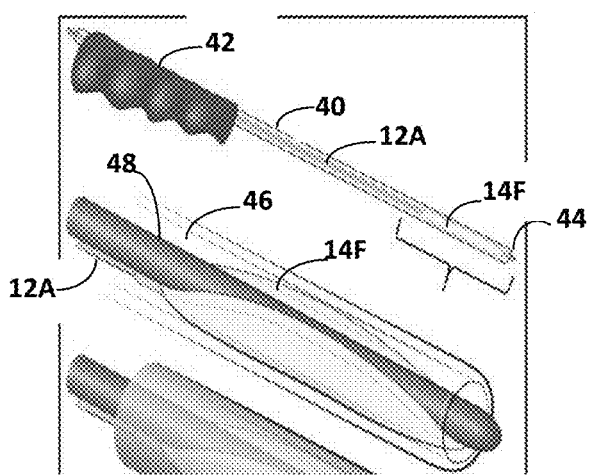
FIG. 9 is a perspective view of insertable components of a system according to an embodiment of the present invention.

The catheter coupled to the inflatable device can be any flexible, non-rigid tubing that is suitable for MICS, although the catheter could be used for other procedures as well. For example, the catheter can have a diameter of between about 22 Fr and 28 Fr. Referring to FIG. 9, in certain embodiments, a system includes a catheter 12A, an inflatable device 14F releasably or fixedly coupled to catheter 12A, and an outer sheath 40 having a proximal end comprising a handle 42, a distal end 44, and a lumen 46 extending longitudinally therebetween. Handle 42 is an ergonomic handle that allows tactile feeling by the operator during insertion of the outer sheath. Catheter 12A and inflatable device 14F are disposed within outer sheath 40 when the inflatable device is in an inactive state. The system can also include a tool 48 that is disposed within lumen 46 of outer sheath 40 to pre-shape the catheter tip before insertion and to provide controlled firmness for proper insertion. Tool 48 allows surgeons to feel when the catheter tip abuts the pericardial wall to avoid injuring surrounding tissue during insertion. The tool can be removed after insertion and the inflatable device can be immediately ready for activation and use.

The catheter or outer sheath can also include a steering mechanism such as a pre-defined distal curved end that can be turned by rotational movement of a proximal handle to ease navigation between anatomical structures. The catheter, or other components of a system, can include markers to indicate proper and improper positioning of the catheter or inflatable device, the depth of insertion of the catheter or the inflatable device, the catheter pull tension or other additional features that can help the operator with handling and maneuvering the insertable components of the system.

Figure 10:
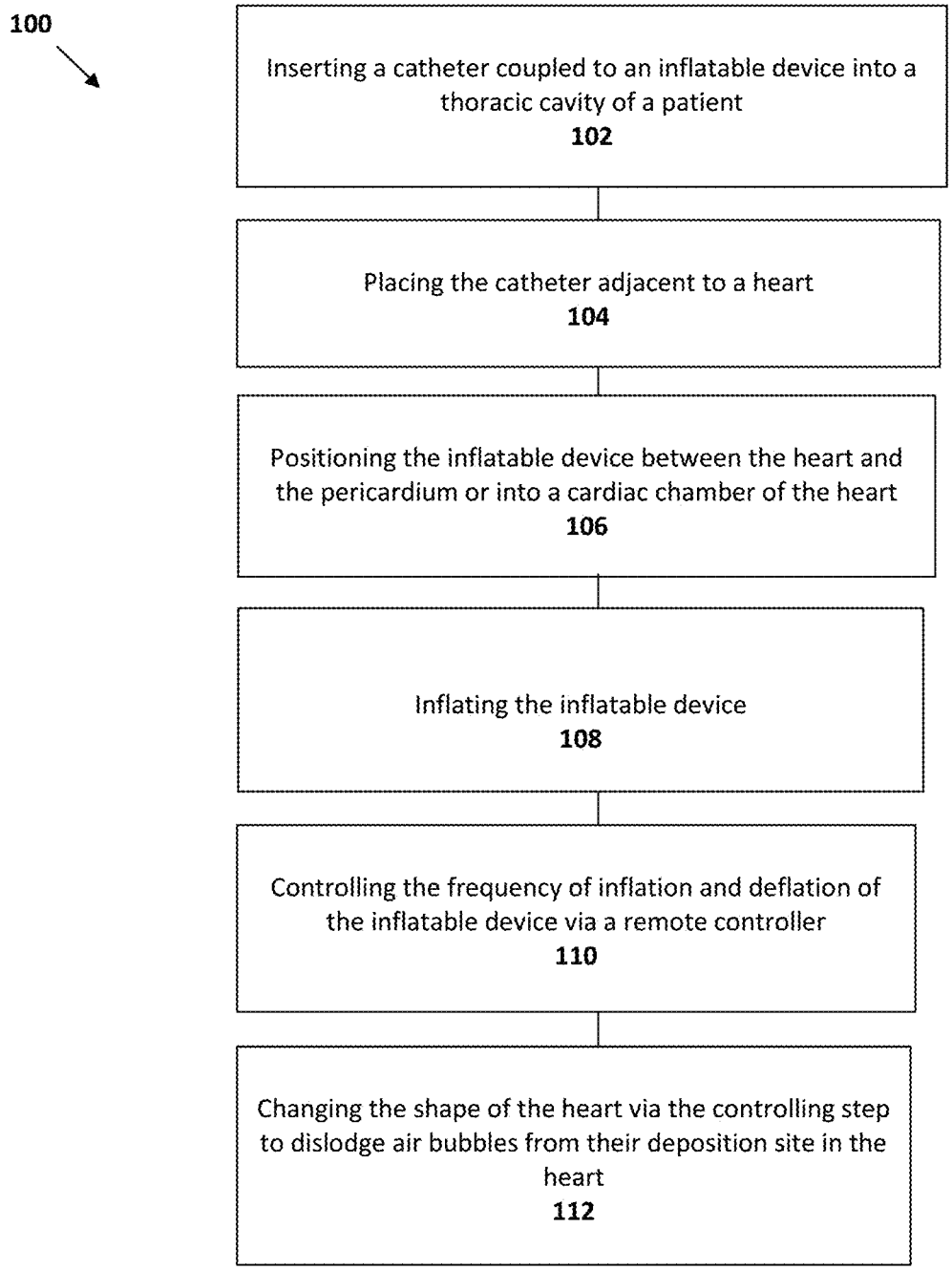
FIG. 10 is a flow diagram illustrating exemplary steps of a method according to an embodiment of the present disclosure.

A cardiac de-airing system can be used to de-air the heart, or a chamber thereof, during or after cardiac surgery. Referring to FIG. 10, method 100 includes inserting a catheter coupled to an inflatable device into a thoracic cavity of a patient 102. Method 100 further includes placing the catheter adjacent to the patient's heart 104 and positioning the inflatable device between the heart and the pericardium 106 or in a cardiac chamber The inflatable device can be placed adjacent to various locations of the heart, including either or both of the left and right cardiac chambers. Further, the implantable device can be positioned, for example, under the heart, laterally, on the anterior surface of the heart or inside a cardiac chamber of the heart. As stated above, placing the inflatable device in the pericardial sac, which is between the heart and the pericardium, effectively self-positions the inflatable device since the pericardium constrains the heart and limits cardiac movement. Further, the lubricated environment between the heart and the pericardium favors insertion of the inflatable device in an inactive state, such as in a flattened configuration. There is also a sufficient gap between the heart and the pericardium to provide space for the inflatable device without requiring dissection of surrounding tissue. Further, the overall sac-like shape of the pericardium surrounding the heart limits dislodgment of the inflatable device beyond the area of interest. In other words, the side of the pericardium opposite the insertion site is intact and therefore closed. In addition, the containment of the heart in its sac may enhance motion transfer from the inflatable device to the targeted area within the heart. Methods can include inserting the catheter, positioning the inflatable device in the target area adjacent to the heart and then connecting the inflatable device to other components, such as a flow line that is connected to a flow control valve. Such steps can make device placement easier.

Referring again to FIG. 10, method 100 includes inflating the inflatable device 108. In certain embodiments, the inflated device is inflated to provide a vermicular movement of the targeted area of the heart at a desired frequency and amplitude of inflation. The inflatable device can be inflated/deflated in a synchronized or asynchronized fashion. Along these lines, method 100 further includes controlling the frequency of inflation and deflation of the inflatable device via a remote controller 110 to change the shape of the heart to dislodge air bubbles from their deposition site in the heart 112. The motion transmitted to the heart by the inflatable device and the blood inside the heart helps move the air bubbles or pools of air inside the cardiac chambers. The air bubbles preferably are moved from areas of lower blood flow towards areas of more active blood flow that remove the air from the cardiac chamber. It should be noted that systems as described herein do not directly evacuate or physically remove air bubbles from the heart such as, for example, ultrasound waves that are applied to the heart to directly affect air bubbles. Rather, systems as described herein mobilize the heart and dislodge air deposited inside the heart so that the air bubbles can be more effectively evacuated through a cardiac incision or a suction line or vent placed in the heart or a blood vessel, such as a left ventricular or aortic vent.

Figure 11:
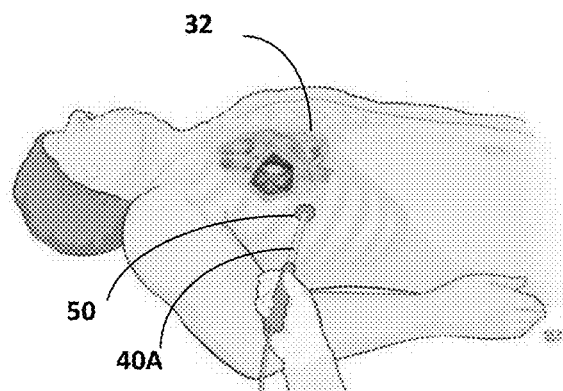
FIGS. 11-12 and FIGS. 13A-C are schematic illustrations depicting an exemplary method and system for de-airing the heart according to an embodiment of the present disclosure.
Figure 12:
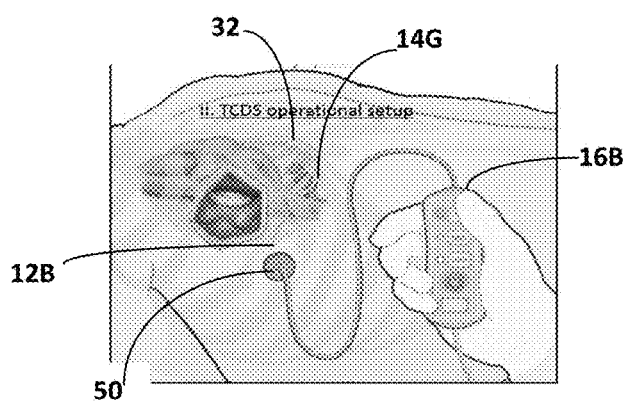
Figures 13A, 13B, 13C:
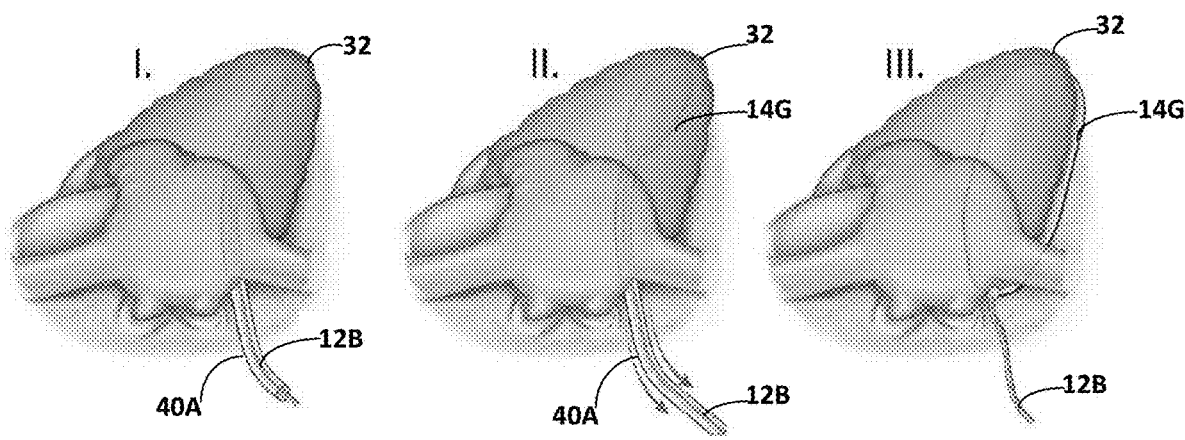

FIGS. 11-12 and FIGS. 13A-C schematically illustrate an exemplary method and system for de-airing a heart. FIGS. 13A-C illustrate only the distal portions of the components of the system. As shown in FIG. 11, an intercostal working port 50 can be placed in the patient's chest to access the heart 32. An outer sheath 40A carrying a catheter 12B coupled to an inflatable device 14G can be inserted through working port 50 and positioned adjacent to the target area of heart 32. As shown in FIG. 12, a remote controller 16B can be in communication with inflatable device 14G (through flow control valves, for example, as described above) and can regulate the inflation and deflation of inflatable device 14G. The remote controller also can be in communication with an external air and vacuum source. Inflation occurs via injection of a fluid or gas, for example, and deflation occurs via application of vacuum, suction or other forms of negative pressure, for example. The inflatable balloon preferably fits into a 5 to 10 mm outer sheath to be suitable for MICS insertion. As seen in FIG. 13A, catheter 12B and inflatable device 14G can be deployed through an outer sheath 40A. The catheter can be malleable via a tool inserted into the lumen of the outer sheath that can enable pre-insertion shaping of the catheter to ensure correct navigation inside the patient's chest and correct area of delivery of the catheter. As stated above, this can secure device placement and avoid cardiac laceration or penetration by a catheter tip prior to activation. As shown in FIG. 13B, once catheter 12B is placed in the proper position adjacent to heart 32, outer sheath 40A can be retrieved proximally to expose inflatable device 14G. As shown in FIG. 13C, once exposed, inflatable device 14G can be inflated and the inflation parameters of the inflatable device can be controlled to achieve a desired configurational change in the heart to dislodge air bubbles from their deposition sites within the heart. The insertable components of a system are sterile and are preferably intended for single use.

Methods as described herein can also include imaging steps, such as using ultrasound or x-rays, echocardiography or fluoroscopy, to view the heart and/or the inflatable device when it is positioned adjacent to the heart and is being inflated or deflated. During use, the inflatable device does not obstruct the view of adjacent anatomical structures. This is due, for example, to the size and configuration of the inflatable device, the fabrication material of the inflatable device, the placement site of the inflatable device in the pericardial sac, and the minimally invasive insertion method.

Systems as described herein are primarily applicable to MICS, including robotic-assisted surgery, but can be used in a variety of surgical procedures. Non-limiting examples of surgical procedures include a heart valve procedure, atrial fibrillation ablation, coronary revascularization, surgery on aorta or major blood vessels, a hybrid cardiac surgical and interventional procedure, ventricular-assist device insertion, and cardiac tumor resection.

Cardiac de-airing systems and methods as disclosed herein can allow surgeons to actively de-air the heart and reduce the time the patient is spent on bypass in addition to the unnecessary cost of the passive "watch and wait" approach currently used. Further, an inflatable device of systems as disclosed herein can be introduced under the heart and maintain its position, without migration, within the partially intact pericardial sac. Systems as disclosed herein enable cardiothoracic surgeons to perform active de-airing of the heart during MICS and traditional cases; reduce surgical time (for total anesthesia, cardiopulmonary bypass (CPB), and/or cross-clamping) thereby improving associated clinical outcomes; and provide a fully measurable, preventive technique of air removal, controlled by the surgeon.

Each of the disclosed aspects and embodiments of the present disclosure may be considered individually or in combination with other aspects, embodiments, and variations of the disclosure. Unless otherwise specified, none of the steps of the methods of the present disclosure are confined to any particular order of performance.

What is claimed is:

1. A system for de-airing the heart in a patient comprising:
   a catheter;
   an inflatable device coupled to the catheter and sized and configured to transmit motion to the patient's heart sufficient to dislodge air bubbles in the heart when the inflatable device is in an active state;
   a remote controller comprising a power source and a processor programmed to inflate and deflate the inflatable device at a frequency range sufficient to dislodge air bubbles in the heart; and
   a flow control valve in communication with the remote controller and the inflatable device.

2. The system of claim 1, further comprising:
   a flow line connected to the flow control valve at one end and the inflatable device at another end; and
   a flow line connectable to the flow control valve at one end and an inflation source at another end.

3. The system of claim 1, further comprising a flow line connected to the flow control valve at one end and connectable to a vacuum source at another end.

4. The system of claim 1, further comprising an outer sheath having a longitudinally extending lumen, the catheter and the inflatable device disposed in the lumen when the inflatable device is in an inactive state.

5. The system of claim 4, further comprising a tool disposable in the lumen of the outer sheath.

6. The system of claim 1, wherein the processor is further programmed to control inflation parameters comprising an onset of inflation and deflation of the inflatable device, a pattern of inflation and deflation of the inflatable device, an amplitude of inflation of the inflatable device, or any combination thereof.

7. The system of claim 1, wherein the inflatable device comprises a plurality of chambers or members, each one of the plurality being selectively and independently inflatable.

8. The system of claim 1, further comprising temperature sensors in communication with the remote controller.

9. The system of claim 1, wherein the remote controller is programmed to automatically adjust inflation parameters based on feedback measurements of the state of inflation of the inflatable device to a certain level or pattern of inflation to maintain that achieves an adequate displacement of the heart to dislodge air bubbles.

10. The system of claim 1, wherein the frequency range is between about 1 Hz and about 100 Hz.

11. A method of de-airing a heart of a patient comprising:
    obtaining the system of claim 1;
    inserting the catheter coupled to the inflatable device into a thoracic cavity of a patient;

positioning the catheter adjacent to the patient's heart;

placing the inflatable device between the heart and the pericardium or into a cardiac chamber of the heart;

inflating the inflatable device;

controlling the frequency of inflation and deflation of the inflatable device via the remote controller and the flow control valve; and dislodging air bubbles from their deposition site in a cardiac chamber of the heart via the controlling step.

12. The method of claim 11, wherein placing the inflatable device comprises placing the inflatable device under the heart on a surface of the heart.

13. The method of claim 11, wherein inflating comprising inflating the inflatable device intermittently, wherein the time period between inflation phases is the same.

14. The method of claim 11, wherein inflating comprises inflating the inflatable device intermittently, wherein the time period between inflation phases is different.

15. The method of claim 11, wherein inserting comprises inserting the catheter through a keyhole incision or through a working port into the intercostal space of the patient's thoracic cavity.

16. The method of claim 11, further comprising detecting the temperature of the heart and adjusting the temperature of an inflation medium used to inflate the inflatable device based on the detection.

17. The method of claim 11, wherein controlling comprises controlling the frequency of inflation and deflation of the inflatable device based on a frequency range sufficient to dislodge air bubbles in the heart.

18. The method of claim 11, further comprising automatically adjusting inflation parameters based on feedback measurements of the state of inflation of the inflatable device to maintain a desired level or pattern of inflation that achieves displacement of the heart to dislodge the air bubbles.

19. The method of claim 11, further comprising measuring the volume of inflation of the inflatable device and dwell time of the inflatable device.

* * * * *